US008210728B2

(12) United States Patent
Tsutsui et al.

(10) Patent No.: US 8,210,728 B2
(45) Date of Patent: Jul. 3, 2012

(54) LED ILLUMINATION APPARATUS WITH FEEDBACK CONTROL MEANS

(75) Inventors: Ryo Tsutsui, Akishima (JP); Yuichiro Matsuo, Hachioji (JP); Yoshihiro Shimada, Sagamihara (JP); Mitsuo Harada, Hachioji (JP)

(73) Assignee: Olympus Corporation, Tokyo (JP)

( * ) Notice: Subject to any disclaimer, the term of this patent is extended or adjusted under 35 U.S.C. 154(b) by 708 days.

(21) Appl. No.: 12/335,954

(22) Filed: Dec. 16, 2008

(65) Prior Publication Data

US 2009/0161358 A1  Jun. 25, 2009

(30) Foreign Application Priority Data

Dec. 19, 2007  (JP) ................. 2007-327789

(51) Int. Cl.
*F21V 7/04* (2006.01)
*F21V 9/10* (2006.01)
*G05D 25/02* (2006.01)

(52) U.S. Cl. ........ 362/552; 362/555; 362/560; 362/575; 362/231; 362/249.12; 315/151

(58) Field of Classification Search .................. 362/552, 362/555, 559, 560, 575, 574, 231, 249.12, 362/800; 315/150, 151
See application file for complete search history.

(56) References Cited

U.S. PATENT DOCUMENTS

| | | | | |
|---|---|---|---|---|
| 4,182,977 A * | 1/1980 | Stricklin, Jr. | ................. | 315/158 |
| 5,404,080 A * | 4/1995 | Quazi | ................. | 315/151 |
| 5,471,052 A * | 11/1995 | Ryczek | ................. | 250/226 |
| 6,153,985 A * | 11/2000 | Grossman | ................. | 315/291 |
| 6,741,351 B2 * | 5/2004 | Marshall et al. | ................. | 356/406 |
| 6,857,762 B2 * | 2/2005 | Shimokawa et al. | ................. | 362/245 |
| 7,009,343 B2 * | 3/2006 | Lim et al. | ................. | 315/150 |
| 7,401,925 B2 * | 7/2008 | Lu | ................. | 353/31 |
| 2005/0047172 A1 * | 3/2005 | Sander | ................. | 362/554 |
| 2005/0190562 A1 * | 9/2005 | Keuper et al. | ................. | 362/325 |
| 2008/0042578 A1 * | 2/2008 | Arai et al. | ................. | 315/32 |
| 2008/0048567 A1 * | 2/2008 | Steele et al. | ................. | 315/151 |
| 2009/0066634 A1 * | 3/2009 | Isobe et al. | ................. | 345/102 |
| 2010/0072900 A1 * | 3/2010 | Deppe | ................. | 315/151 |
| 2010/0156302 A1 * | 6/2010 | Park et al. | ................. | 315/151 |

FOREIGN PATENT DOCUMENTS

| JP | 2005235954 | 9/2005 |
|---|---|---|
| JP | 2005321453 | 11/2005 |

* cited by examiner

*Primary Examiner* — Ismael Negron

(74) *Attorney, Agent, or Firm* — Pillsbury Winthrop Shaw Pittman, LLP

(57) ABSTRACT

An illumination apparatus that includes a plurality of LEDs of different center emission wavelengths, a photodetector, a path sharing device for introducing light emitted from the plurality of LEDs into the common optical path, a light-introducing device located on the common optical path to introduce part of the light emitted from the plurality of LEDs passing through the common optical path into the photodetector, a feedback controller controlling turning-on states of the LEDs over preset states in accordance with the amount of light emitted from the plurality of LEDs detected by the photodetector, and an illumination light supplying device located on the common optical path to supply light which is emitted from the plurality of LEDs to pass through the common optical path and is not introduced into the photodetector through the light-introducing device, as illumination light for a cellular analysis.

11 Claims, 5 Drawing Sheets

LED ILLUMINATION APPARATUS WITH FEEDBACK CONTROL MEANS

This application claims benefits of Japanese Patent Application No. 2007-327789 filed in Japan on Dec. 19, 2007, the contents of which are incorporated herein by reference.

BACKGROUND OF THE INVENTION

1. Field of the Invention

This invention relates to an illumination apparatus used for a cellular analysis apparatus such as a microscope, and more specifically, to an illumination apparatus provided with light sources for irradiating a cell or nucleus labeled by fluorescence with excitation light.

2. Description of Related Art

Conventional illumination apparatuses have long been applied to general illumination, decoration, advertisement, warning, introduction, and illumination for amusement. Such illumination apparatuses are available with light sources of types, such as filament lamps, halogen lamps, xenon lamps, mercury lamps, mercury xenon lamps, and fluorescent lamps, or with various light sources which are not limited to these types. These light sources, when used in the illumination apparatus for the cellular analysis apparatus, have the following many disadvantages.

For example, the light source, such as a halogen lamp or filament lamp, generates undesirable heat for maintaining a state of a cell and light produced by this light source is limited to white or yellow light. Hence, the illumination apparatus using such light sources requires lenses and filtering systems in considerable numbers in order to produce light of various wavelengths (colors) as excitation light used for the analysis of the cell. As a result, time during which a desirable state for the observation of the cell can be maintained is appreciably reduced and cost is materially increased. Further, each of the conventional light sources mentioned above has highly limited product life, which is about 2000 hours. Still further, in the ambiance that is exceedingly subject to shock and vibration, the light source is liable to be damaged.

However, light-emitting diode (LED) light sources have made great strides in recent years and are the ones that have high return on investment, replacing the conventional light sources. The LED light source, in contrast with the conventional light source, has distinct advantages that the product life of most light sources is as long as ten thousand hours or more and in addition, the consumption of electric energy relative to the intensity of given light is low. Moreover, the LED light source also has advantages that durability relative to shock and vibration is high, a heat loss is small, response time for switching is very short, and the selection of illumination color is wide.

For a conventional illumination apparatus in which the LED light source is used in the cellular analysis apparatus such as the microscope, for example, Japanese Patent Kokai No. 2005-321453 discloses an illumination apparatus in which the light source is constructed with a plurality of light-emitting diodes emitting light of different wave-lengths so that light from the plurality of light-emitting diodes is introduced into a common optical path. This illumination apparatus is such that the amount of light of each of the light-emitting diodes can be adjusted through the operation of an operation section.

In the observation and analysis of the cell, it is required that changes of the location, shape, and intensity of fluorescent light of a substance for its object are quantitatively found from an image, and thus it is essential that the amount of light of each of illumination light sources used for the observation and analysis of the cell is kept constantly from the start of the observation to the end.

However, the LED light source has the drawback that although the LED light source is smaller in heat loss than other light sources, its amount of light is changed because of the influence of heat generated from the ambience of the LED light source and the LED light source itself. In addition, due to the deterioration of the LED light source itself, the change of the amount of light may be brought about.

Also, as the conventional light source other than the LED light source, for example, in a microscope using a plurality of laser light sources, there is a light source which has a detection means for detecting the amount of laser light and a light-adjusting means for adjusting the amount of laser light in accordance with the amount of light obtained by the detection means (refer to, for example, Japanese Patent Kokai No. 2005-235954). This microscope is constructed so that light from the laser light sources is split into two optical paths, one of which is directed toward a specimen and the other is directed toward the detection means, through a beam splitter placed on the optical axis and the amount of light directed toward the detection means is detected.

SUMMARY OF THE INVENTION

The illumination apparatus for the cellular analysis apparatus according to the present invention, which is the illumination apparatus supplying the cellular analysis apparatus with illumination light through a common optical path, comprises a plurality of LEDs of different center emission wavelengths, a photodetector, a path sharing means for introducing light emitted from the plurality of LEDs into the common optical path, a light-introducing means located on the common optical path to introduce part of the light emitted from the plurality of LEDs passing through the common optical path into the photodetector, a feedback controller controlling turning-on states of the LEDs over preset states in accordance with the amount of light emitted from the plurality of LEDs detected by the photodetector, and an illumination light supplying means located on the common optical path to supply light which is emitted from the plurality of LEDs to pass through the common optical path and is not introduced into the photodetector through the light-introducing means, as illumination light for a cellular analysis.

In the illumination apparatus for the cellular analysis apparatus of the present invention, it is desirable that the light-introducing means is a reflecting member reflecting the part of the light emitted from the plurality of LEDs toward the photodetector.

In the illumination apparatus for the cellular analysis apparatus of the present invention, it is desirable that the reflecting member is located so that, of beams of the light emitted from the plurality of LEDs, a part of a light beam traveling through an outer portion of a light beam effective for illumination of a cell is reflected.

In the illumination apparatus for the cellular analysis apparatus of the present invention, it is desirable that the reflecting member is a mirror, a metallic member having a flat surface processed as a specular reflecting surface, or a glass plate.

In the illumination apparatus for the cellular analysis apparatus of the present invention, it is desirable that the reflecting member is such that a position relative to the common optical path is adjustable and the amount of light where the part of the light emitted from the plurality of LEDs is reflected toward the photodetector is adjustable by adjusting the position relative to the common optical path.

In the illumination apparatus for the cellular analysis apparatus of the present invention, it is desirable to further comprise an optical transmission fiber transmitting light reflected by the reflecting member to the photodetector.

In the illumination apparatus for the cellular analysis apparatus of the present invention, it is desirable to further comprise an optical fiber having one entrance end and two exit ends into which the exit side is bifurcated, in which the entrance end of the optical fiber is located to introduce all the light emitted from the plurality of LEDs on the common optical path into the optical fiber, while the exit ends of the optical fiber are constructed so that one exit end constitutes the light-introducing means and the other exit end constitutes the illumination light supplying means.

In the illumination apparatus for the cellular analysis apparatus of the present invention, it is desirable that the feedback controller is constructed so that control of the turning-on states of the LEDs over the preset states is made by adjusting amounts of electric currents supplied to the LEDs.

In the illumination apparatus for the cellular analysis apparatus of the present invention, it is desirable to have an overcurrent preventing control function making control so that overcurrent is prevented from flowing through any of the plurality of LEDs.

According to the present invention, the illumination apparatus for the cellular analysis apparatus is obtained in which the loss of light supplied for cell irradiation is kept to a minimum, the amount of light of the LED light sources is automatically maintained constant, and changes of the location, shape, and intensity of fluorescent light of a substance for its object can be quantitatively found from an image.

These and other features and advantages of the present invention will become apparent from the following detailed description of the preferred embodiments when taken in conjunction with the accompanying drawings.

DETAILED DESCRIPTION OF THE PREFERRED EMBODIMENTS

Figure 1:
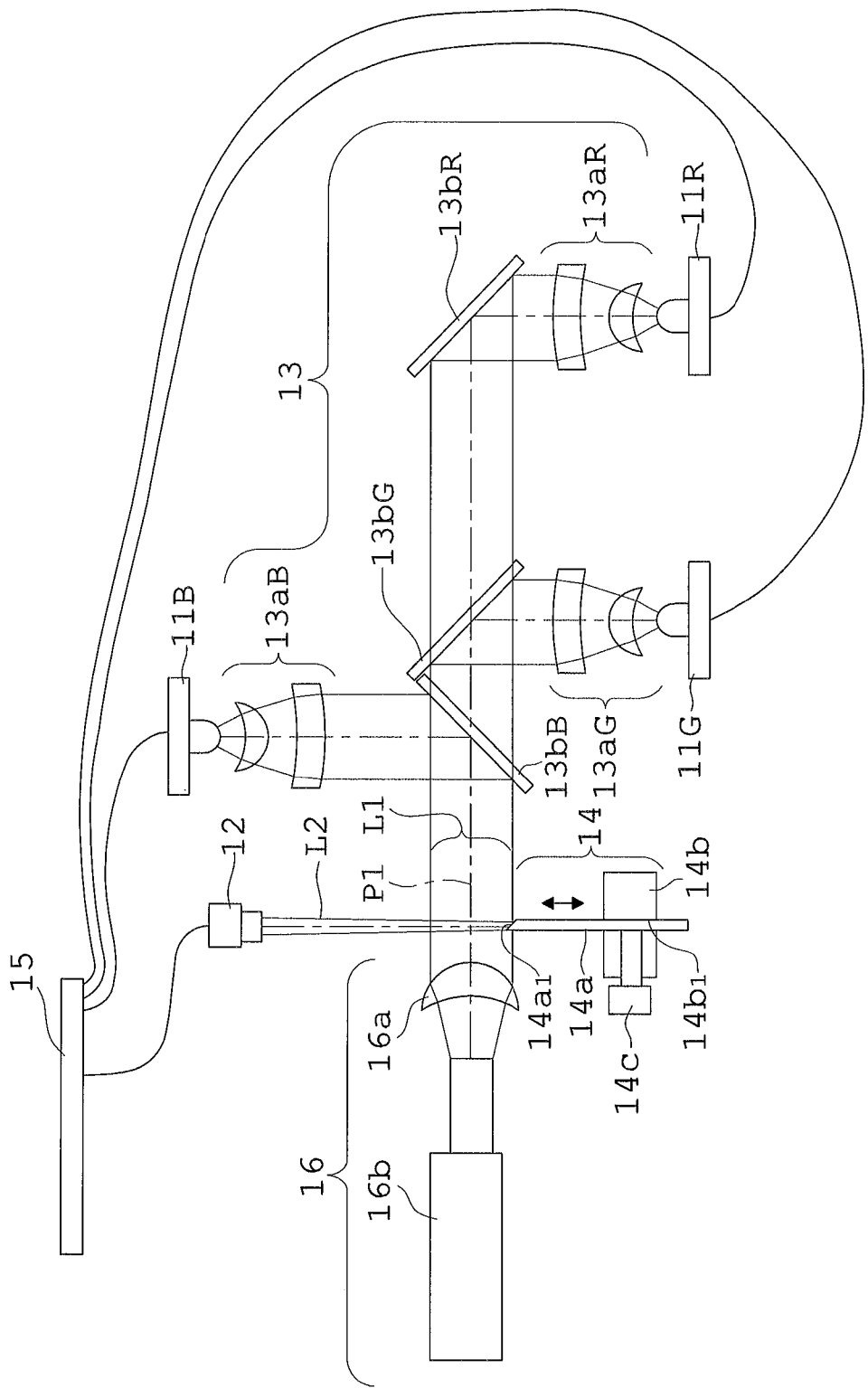
FIG. 1 is an explanatory view showing a schematic structure of the illumination apparatus for the cellular analysis apparatus according to a first embodiment of the present invention.

Before undertaking the description of the embodiments, the structure, function, and effect of the present invention will be explained.

The illumination apparatus for the cellular analysis apparatus, which is the illumination apparatus supplying the cellular analysis apparatus with illumination light through a common optical path, includes a plurality of LEDs of different center emission wavelengths, a photodetector, a path sharing means, a light-introducing means, a feedback controller, and an illumination light supplying means. The path sharing means is constructed with, for example, a collector lens and a dichroic mirror so that light emitted from a plurality of LEDs of different center emission wavelengths is introduced into the common optical path. The light-introducing means is constructed with, for example, a reflecting member such as a mirror and is located on the common optical path. The light-introducing means is such that part of light emitted from the plurality of LEDs passing through the common optical path is introduced into the photodetector. In this case, for light to be introduced into the photodetector, it is good practice to use light in a region deviating from a light beam effective for illumination of the cell. For example, when the light-introducing means is constructed with the reflecting member, the reflecting member is located so that, of beams of the light from the plurality of LEDs, a part of a light beam traveling through the outer portion of a light beam effective for the illumination of the cell is reflected. The illumination light supplying means is constructed with, for example, an imaging lens and an optical fiber and is located on the common optical path. Light which is emitted from the plurality of LEDs to pass through the common optical path and is not introduced into the photodetector through the light-introducing means (namely, is within the limit of the diameter of a light beam effective for the illumination of the cell) is supplied as illumination light for the cellular analysis. The feedback controller is such that, in accordance with the amount of light emitted from the plurality of LEDs detected by the photodetector, for example, the electric currents flowing through the LEDs are controlled and thereby the turning-on states of the LEDs are controlled over (adjusted to) preset states.

When the illumination apparatus for the cellular analysis apparatus is constructed as mentioned above, the light emitted from the plurality of LEDs of different center emission wavelengths is introduced into the common optical path through the path sharing means. The light thus introduced is such that its part is introduced through the light-introducing means into the photodetector, through which the amount of light is detected, and remaining light is supplied to the cellular analysis apparatus through the illumination light supplying means. At this time, data of the amount of light detected by the photodetector are sent to the feedback controller. In the feedback controller, for example, the electric currents flowing through the LEDs are controlled in accordance with the amount of light detected through the photodetector, and thereby the turning-on states of the LEDs is controlled (adjusted) to maintain the preset states. Consequently, according to the illumination apparatus for the cellular analysis apparatus, it becomes possible that the amount of light of the LED light sources is kept constantly and the changes of the location, shape, and intensity of fluorescent light of the substance for its object are quantified from an image.

According to the illumination apparatus for the cellular analysis apparatus, of beams of the light from the plurality of LEDs, a part of a light beam traveling through the outer portion of a light beam effective for the illumination of the cell is introduced into the photodetector, and thereby the loss of light effective for the illumination of the cell can be kept to a minimum.

Also, in the feedback controller used in the illumination apparatus for the cellular analysis apparatus, it is desirable to control the electric currents so that overcurrents do not flow through the LEDs. By doing so, for example, even when data of the amount of light of the LEDs detected by the photodetector have extremely low values, the damage of the LEDs caused by the overcurrents can be obviated.

In accordance with the drawings, the embodiments of the present invention will be explained in detail below.

First Embodiment

Figure 2:
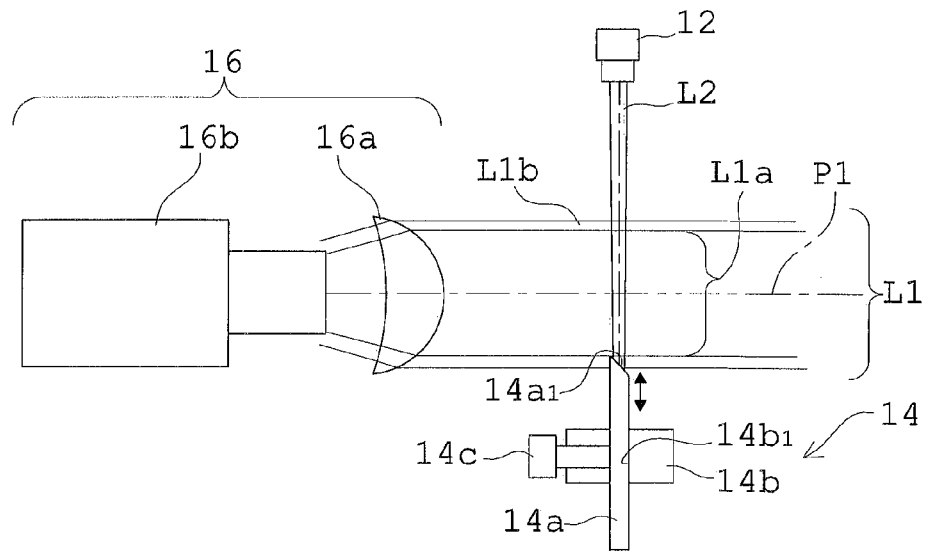
FIG. 2 is a partially enlarged view showing a relative positional relationship of a light-introducing means concerning light passing through a common optical path, emitted from a plurality of LEDs, in the illumination apparatus for the cellular analysis apparatus of FIG. 1.
Figures 3A, 3B:
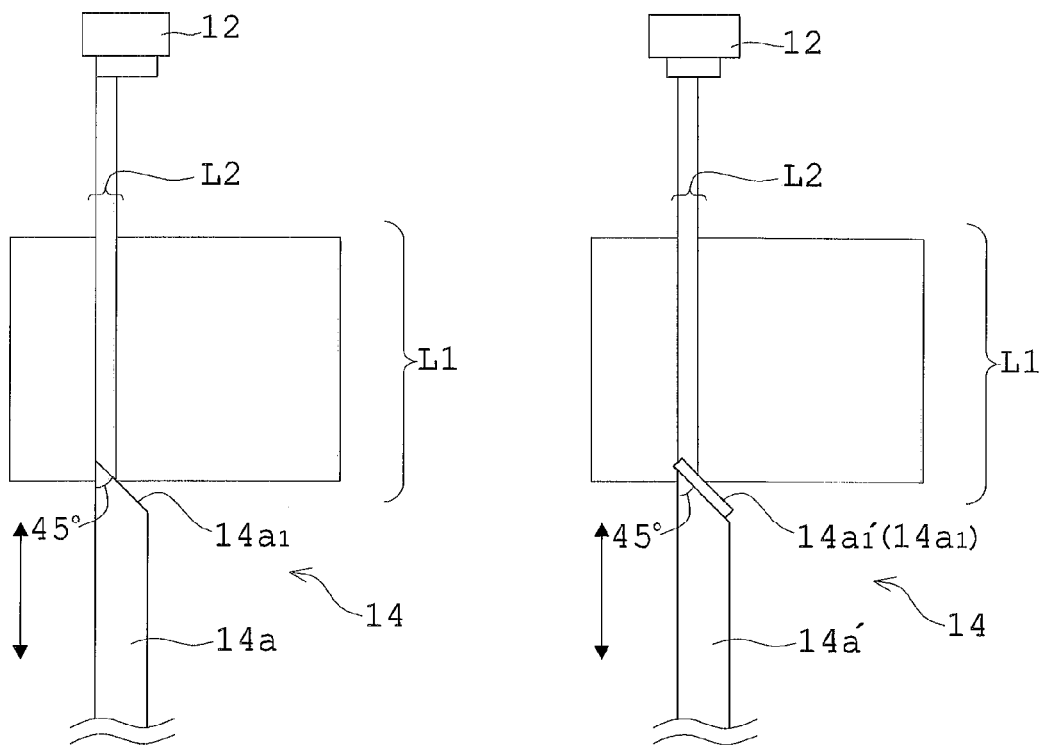
FIGS. 3A, 3B, and 3C are enlarged views showing structures of the light-introducing means in the illumination apparatus for the cellular analysis apparatus of FIG. 1, which are examples different from one another.
Figure 3C:
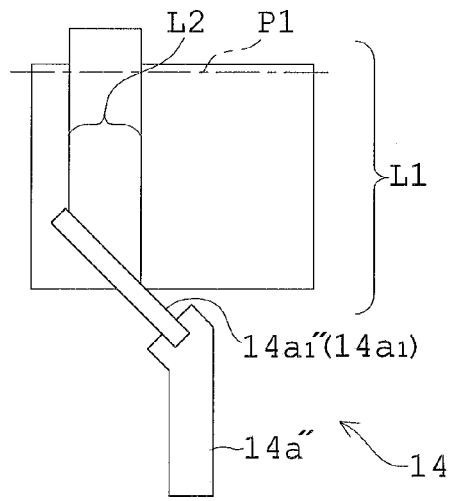
Figures 4A, 4B:
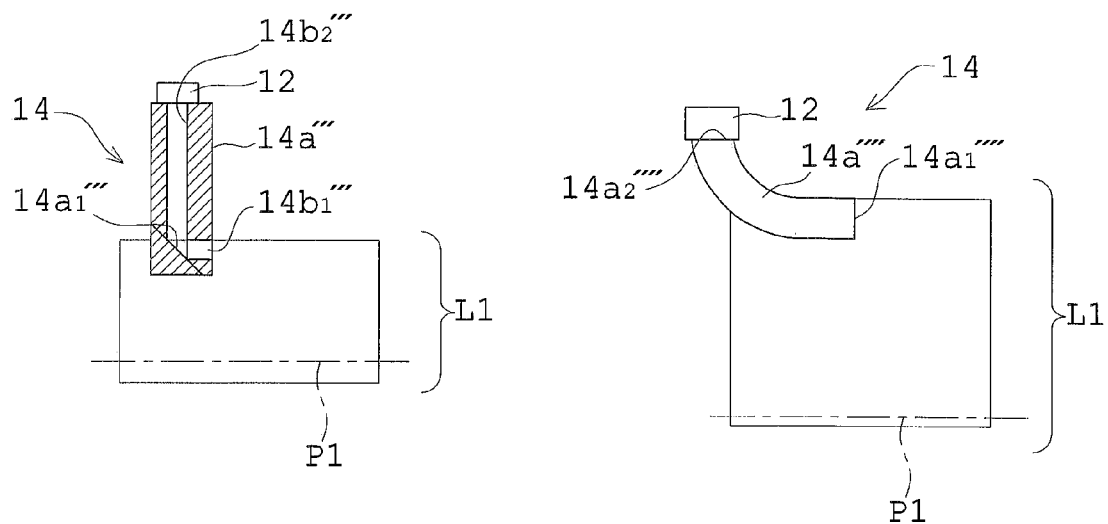
FIGS. 4A and 4B are explanatory views showing structures of other modified examples of the light-introducing means in the illumination apparatus for the cellular analysis apparatus of FIG. 1, which are different from each other.
Figure 5:
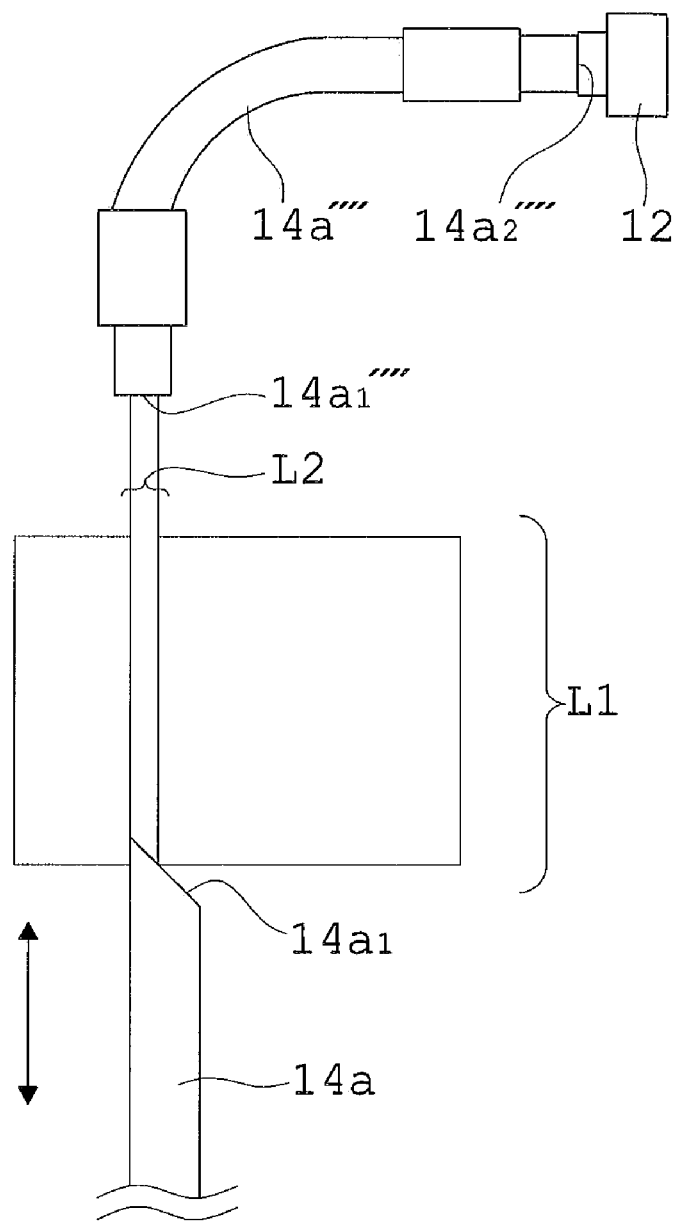
FIG. 5 is an explanatory view showing the structure of still another modified example of the light-introducing means in the illumination apparatus for the cellular analysis apparatus of FIG. 1.

FIG. 1 shows a schematic structure of the illumination apparatus for the cellular analysis apparatus according to the first embodiment of the present invention. FIG. 2 shows a relative positional relationship of a light-introducing means concerning light passing through a common optical path, emitted from a plurality of LEDs, in the illumination apparatus for the cellular analysis apparatus of FIG. 1. FIGS. 3A, 3B, and 3C illustrate structures of the light-introducing means in the illumination apparatus for the cellular analysis apparatus of FIG. 1. FIGS. 4A and 4B illustrate structures of other modified examples of the light-introducing means in the illumination apparatus for the cellular analysis apparatus of FIG. 1. FIG. 5 shows the structure of still another modified example of the light-introducing means in the illumination apparatus for the cellular analysis apparatus of FIG. 1.

The illumination apparatus for the cellular analysis apparatus of the first embodiment is the illumination apparatus for a microscope apparatus in which a specimen is irradiated with light from a plurality of LEDs of different center wavelengths as light sources so that the observation of the specimen is carried out, and includes a red LED 11R, a green LED 11G, and a blue LED 11B which have different center emission wavelengths; a photodetector 12; a path sharing means 13; a light-introducing means 14, a feedback controller 15; and an illumination light supplying means 16. The photodetector 12 is constructed with a light-receiving sensor. The path sharing means 13 has collector lenses 13aR, 13aG, and 13aB and dichroic mirrors 13bR, 13bG, and 13bB.

The collector lenses 13aR, 13aG, and 13aB are constructed so that light emitted from the red LED 11R, the green LED 11G, and the blue LED 11B is converted into parallel rays in which the diameters of light beams are almost the same. The dichroic mirror 13bR is located on the exit optical path of the red LED 11R and is constructed to reflect light of red wavelength only. The dichroic mirror 13bG is located at a position where the transmission optical path of the dichroic mirror 13bR intersects with the exit optical path of the green LED 11G and is constructed to reflect light of green wavelength only and to transmit light of wavelength longer than the green wavelength (for example, the light of red wavelength). The dichroic mirror 13bB is located at a position where the transmission optical path of the dichroic mirror 13bG intersects with the exit optical path of the blue LED 11B and is constructed to reflect light of blue wavelength only and to transmit light of wavelength longer than the blue wavelength (for example, light of green and red wavelengths).

In this way, the path sharing means 13 has the function of converting the light emitted from the red LED 11R, the green LED 11G, and the blue LED 11B into parallel rays to superpose the parallel rays on the common optical path.

The illumination light supplying means 16 is constructed with an imaging lens 16a and an optical fiber 16b. The imaging lens 16a is provided so that light which is converted into parallel beams through the collector lens 13aR, 13aG, and 13aB to pass through the common optical path and is not introduced into the photodetector through the light-introducing means is rendered incident on the entrance end surface of the optical fiber 16b. The exit-side end of the optical fiber 16b is connected to a microscope (omitted from the figure) as the cellular analysis apparatus.

The light-introducing means, as shown in FIG. 3A, is constructed so that the tip of a bar-shaped member 14a made of metal such as stainless steel is cut at angle of 45 degrees and in addition, an end surface thus cut is fabricated into a specular surface to thereby provide a reflecting member having a reflecting surface $14a_1$. The light-introducing means 14, as shown in FIG. 2, is located at a position where, of a beam L1 of the light emitted from the red LED 11R, the green LED 11G, and the blue LED 11B which pass through the common optical path, a part of a beam L1b of light traveling through the outer portion of a light beam effective for the illumination of the cell can be reflected by the reflecting surface $14a_1$ toward the photodetector 12. In FIG. 2, reference symbol L2 denotes a beam of light reflected through the light-introducing means 14 toward the photodetector 12. The reflecting member is moved perpendicular to an optical axis P1 of the common optical path through a guide hole $14b_1$ and a screw 14c which are provided to a supporting member 14b, and can be fixed at a desired position. As the reflecting member is moved close to the optical axis P1 of the common optical path, the area of the reflecting surface $14a_1$ admitted into the common optical path enlarges to increase the amount of light reflected toward the photodetector 12, and when the reflecting member is moved closer to the optical axis P1 from some position, the light is reflected by the entire reflecting surface $14a_1$. Conversely, as the reflecting member is moved far away from the optical axis P1 of the common optical path, the area of the reflecting surface $14a_1$ admitted into the common optical path diminishes to reduce the amount of light reflected toward the photodetector 12, and when the reflecting member is moved further away from some position, the reflecting surface $14a_1$ deviates from the common optical path and the amount of light reflected toward the photodetector 12 is reduced to zero. Also, in order to prevent the reflecting member from adversely affecting the amount of illumination light for the cellular analysis supplied to the microscope omitted from the figure, it is desirable that the position of the reflecting member is adjusted so that only the part of the light beam L1b traveling through the outer portion of a light beam L1a effective for the illumination of the cell is reflected by the reflecting surface $14a_1$ toward the photodetector 12. However, the area of the reflecting surface $14a_1$ is much smaller than the sectional area of the light beam L1a effective for the illumination of the cell, and thus even when the reflecting surface $14a_1$ of the reflecting member is brought close to the optical axis P1 of the common optical path to reflect the part of the light beam L1a effective for the illumination of the cell toward the photodetector 12, the amount of light used for the illumination of the cell is little adversely affected. In addition, the optical fiber 16b is used for the illumination light supplying means 16, and hence even though the part of the light beam L1a effective for the illumination of the cell is not introduced into the illumination light supplying means 16 by the reflecting surface $14a_1$, light incident on the entrance end surface of the optical fiber 16b is such as to repeat the reflection inside the optical fiber 16b and thereby to keep the uniformity of illumination light supplied to the microscope.

The feedback controller 15 is connected to the photodetector 12 and the plurality of LEDs 11R, 11G, and 11B. The feedback controller 15 is constructed so that, in accordance with the amount of light emitted from each of the plurality of LEDs 11R, 11G, and 11B detected by the photodetector 12, the electric current flowing through each LED is controlled and thereby the turning-on state of the LED is controlled over (adjusted to) the preset state.

As for the rest, it is possible that the illumination apparatus for the cellular analysis apparatus of the first embodiment is connected to an LED turning-on state commanding input means omitted from the figure. The LED turning-on state commanding input means is provide with input devices such as a display screen and a keyboard so that a preset turning-on state can be designated for every LED. The feedback controller 15 controls the preset turning-on state in each LED in accordance with a command value input through this LED turning-on state commanding input means.

When the illumination apparatus for the cellular analysis apparatus of the first embodiment constructed as mentioned above is used to provide illumination for the cellular analysis, the position of the reflecting surface 14a, of the reflecting member relative to the common optical path is previously adjusted and at the same time, the amount of light received by the photodetector 12 is adjusted. Specifically, for example, any one of the LEDs is turned on by the electric current of about a half of the maximum output through the LED turning-on state commanding input means and at the same time, the reflecting member is moved perpendicular to the optical axis P1 of the common optical path. By holding light reflected by the reflecting surface $14a_1$ of the reflecting member to enter a measurable region of a photosensor constituting the photodetector 12, the position of the reflecting surface $14a_1$ of the reflecting member is adjusted so that the amount of light received by the photosensor reaches a preset value.

The other LEDs are likewise turned on successively and are set so that the light enter the measurable range of the photosensor.

After the position of the reflecting surface $14a_1$ of the reflecting member is adjusted, the preset turning-on state is designated for every LED through the LED turning-on state commanding input means.

After such adjustments, individual LEDs are used as the light sources of the illumination apparatus for the cellular analysis apparatus. Light emitted from the red LED 11R, the green LED 11G, and the blue LED 11B is converted through the path sharing means 13 into parallel rays, which pass through the common optical path. Of the light beam L1 passing through the common optical path, a part of the light beam L1b traveling through the outer portion of a light beam effective for the illumination of the cell is reflected by the reflecting surface $14a_1$ of the bar-shaped member 14a constituting the light-introducing means 14 and is directed toward, and received by, the photodetector 12. Of the light beam L1 which is not introduced into the photodetector 12 through the light-introducing means 14 and passes through the common optical path, the light beam L1a effective for the illumination of the cell is incident on the entrance end surface of the optical fiber 16 through the imaging lens 16a and is supplied, as illumination light, to the microscope for the cellular analysis apparatus, not shown, through the exit-side end.

During this time, data of the amount of light received through the photodetector 12 are supplied to the feedback controller 15. The feedback controller 15 compares the data value of the amount of light emitted from each of the plurality of LEDs 11R, 11G, and 11B detected through the photodetector 12 with the command value input through the LED turning-on state commanding input means. In accordance with this comparison result, the electric current flowing through each LED is controlled and thereby the turning-on state of the LED is controlled over (adjusted to) the preset state.

In the illumination apparatus for the cellular analysis apparatus of the first embodiment, as mentioned above, the outputs of the plurality of LEDs are detected and the feedback control is performed, thereby making the amount of light output from the LEDs always constant. According to the illumination apparatus for the cellular analysis apparatus, therefore, when the LEDs are used as the light sources of the microscope, an illumination condition can be kept constantly even in an experimental system for observing the growth of the cell for a long period of time, and quantification can be brought to observation data, extending from the start of the observation to the end. In other words, since the feedback control of the light source is performed, the quantification can also be brought to experimental data secured on different dates and hours if experimental conditions are the same.

Also, the light-introducing means 14 may be constructed so that a mirror or a glass plate is used for the reflecting surface $14a_1$. For example, in the light-introducing means 14, as shown in FIG. 3B, the reflecting surface $14a_1$ may be constructed by providing a mirror $14a_1'$ on the end surface that the tip of a bar-shaped member $14a'$ is cut at 45 degrees.

Alternatively, the light-introducing means 14, as shown in FIG. 3C, instead of cutting the tip of the bar-shaped member at 45 degrees, is designed so that a glass plate is inclined at 45 degrees with respect to the optical axis of the common optical path and is held by a bar shaped member $14a''$, and a surface $14a_1''$ of this glass plate may be thought of as the reflecting surface $14a_1$.

Alternatively, the light-introducing means 14, as illustrated in FIG. 4A, may be constructed so that a cylindrical member $14a'''$ extending from a part of the common optical path to the photodetector 12 has a first hole $14b_1'''$ parallel to the optical axis P1 of the common optical path, a reflecting surface $14a_1'''$ (corresponding to the reflecting surface $14a_1$) provided at an inclination of 45 degrees with respect to the optical axis P1 of the common optical path and reflecting light passing through the first hole $14b_1'''$, and a second hole $14b_2'''$ provided perpendicular to the optical axis P1 of the common optical path and introducing light reflected by the reflecting surface $14a_1'''$ toward the photodetector 12. In this way, relative positions of the reflecting surface $14a_1'''$ and the photodetector 12 are fixed and hence it becomes unnecessary to adjust the relative positions of the light-introducing means 14 and the photodetector 12. Also, the second hole $14b_2'''$ may be provided with a fiber.

Alternatively, the light-introducing means 14, as illustrated in FIG. 4B, may be constructed with a fiber $14a''''$, an entrance end surface $14a_1''''$ of which faces a part of the common optical path and an exit end surface $14a_2''''$ of which is connected to the photodetector 12. In this way, relative positions of the exit end surface $14a_2''''$ and the photodetector 12 are fixed and hence the adjustments of the relative positions of the light-introducing means 14 and the photodetector 12 become unnecessary. Moreover, the number of degrees of placement freedom of the photodetector 12 is increased.

Further, the light-introducing means 14, as shown in FIG. 5, for example, in addition to the structure shown in FIG. 3A, may be constructed with the fiber $14a''''$, the entrance end surface $14a_1''''$ of which faces an optical path reflected by the reflecting surface $14a_1$ and the exit end surface $14a_2''''$ of which is connected to the photodetector 12. In this case also, the number of degrees of placement freedom of the photodetector 12 is increased.

Second Embodiment

Figure 6:
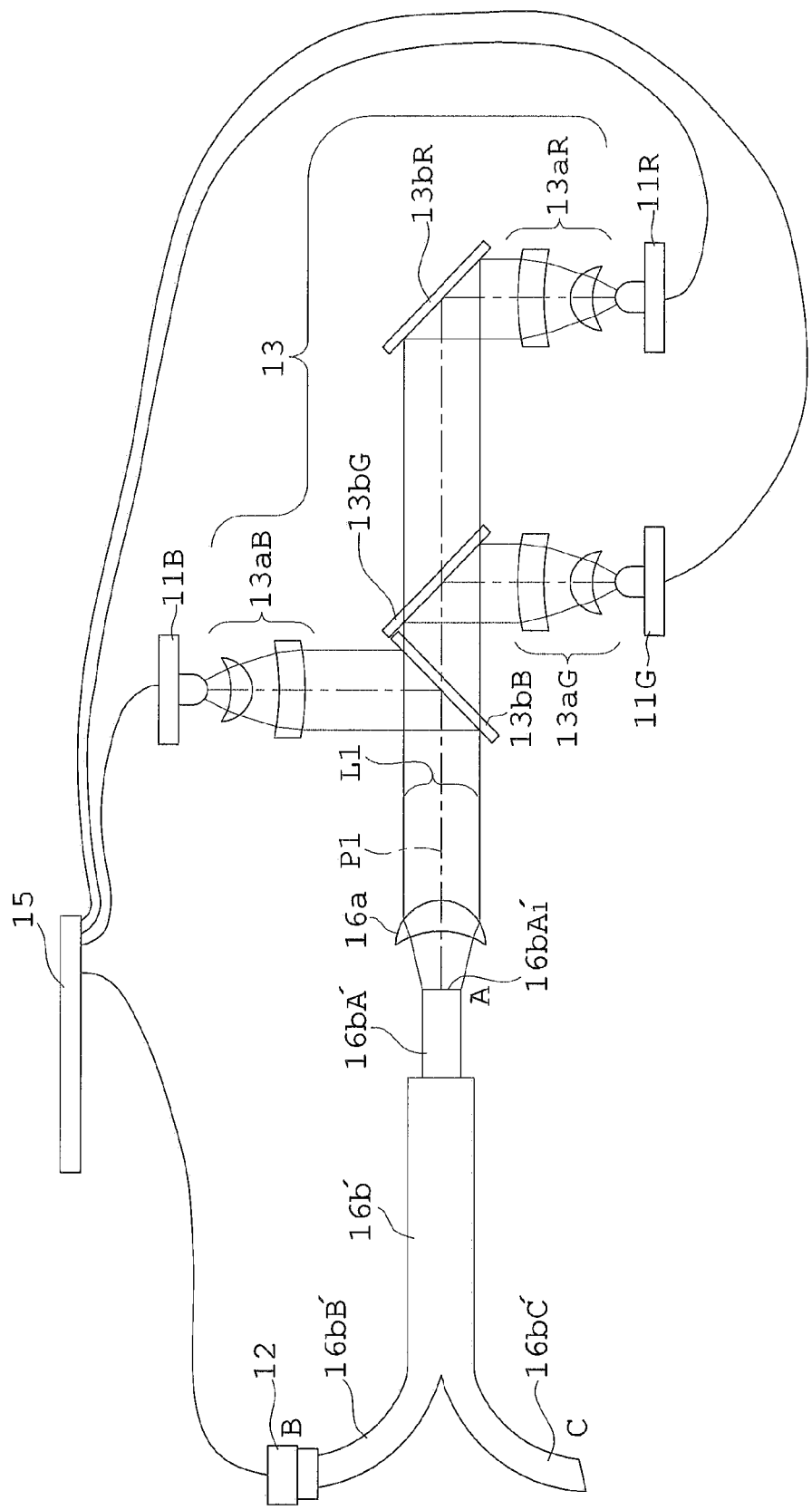
FIG. 6 is an explanatory view showing a schematic structure of the illumination apparatus for the cellular analysis apparatus according to a second embodiment of the present invention.

FIG. 6 shows a schematic structure of the illumination apparatus for the cellular analysis apparatus according to the second embodiment of the present invention. The illumination apparatus for the cellular analysis apparatus of the second embodiment, instead of including the optical fiber 16*b* and the light-introducing means 14 in the illumination apparatus for the cellular analysis apparatus of the first embodiment, is constructed to include an optical fiber 16*b*' having one entrance end 16*b*A' and two exit ends 16*b*B' and 16*b*C' into which the exit side is bifurcated.

The entrance end 16*b*A' of the optical fiber 16*b*' is located, with an entrance end surface 16*b*A$_1$' facing the imaging position of the imaging lens 16*a*, to introduce all the light emitted from the plurality of LEDs on the common optical path into the optical fiber. One exit end 16*b*B' of the optical fiber is connected to the photodetector 12 and has the function as the light-introducing means. The other exit end 16*b*C' of the optical fiber is connected to the microscope, not shown, and has the function as the illumination light supplying means. Other features are almost the same as in the illumination apparatus for the cellular analysis apparatus of the first embodiment.

According to the illumination apparatus for the cellular analysis apparatus of the second embodiment constructed as mentioned above, the optical fiber 16*b*' has the functions of the light-introducing means and the illumination light supplying means at the same time, and thus the number of parts can be reduced. Since the optical fiber 16*b*' functions as the light-introducing means, it becomes unnecessary to adjust the relative positions with the photodetector 12 as in the case where the reflecting member shown in FIG. 3A is used. Moreover, the number of degrees of placement freedom of the photodetector 12 is increased. Further, according to the illumination apparatus for the cellular analysis apparatus of the second embodiment, the optical fiber 16*b*' is designed so that the area of the exit end 16*b*B' connected to the photodetector 12 and functioning as the light-introducing means is slightly larger than that of the exit end 16*b*C' connected to the microscope and functioning as the illumination light supplying means, thereby allowing the loss of light effective for the illumination of the cell to be kept to a minimum. Other functions and effects are almost the same as in the illumination apparatus for the cellular analysis apparatus of the first embodiment.

As will be evident from the above description, the present invention is useful for the fields of biology and medicine in which faint light is used to carry out the observation and analysis of the cell.

What is claimed is:

1. An illumination apparatus for a cellular analysis apparatus, which is the illumination apparatus supplying the cellular analysis apparatus with illumination light through a common optical path, the illumination apparatus comprising:
   a plurality of LEDs of different center emission wavelengths,
   a photodetector,
   path sharing means for introducing light emitted from the plurality of LEDs into the common optical path,
   light-introducing means located on the common optical path to intercept a portion of the light emitted from the plurality of LEDs and travelling along the common optical path, for introducing the intercepted portion of light into the photodetector,
   a feedback controller for controlling turning-on states of the LEDs over preset states in accordance with an amount of light emitted from the plurality of LEDs detected by the photodetector, and
   illumination light supplying means located on the common optical path downstream from the light-introducing means, to receive and supply light emitted from the plurality of LEDs and travelling along the common optical path excluding the intercepted portion of light intercepted by the light-introducing means, as illumination light for a cellular analysis,
   wherein the light-introducing means is a reflecting member that reflects the intercepted portion of light toward the photodetector, and
   wherein a position of the reflecting member relative to the common optical path is adjustable and an amount of the intercepted portion of light reflected toward the photodetector is adjustable by adjustment of the position of the reflecting member relative to the common optical path.

2. The illumination apparatus for a cellular analysis apparatus according to claim 1, wherein the reflecting member is located in such a manner as to reflect, of rays of the light emitted from the plurality of LEDs, a part of rays that travel through a region outside of an effective light beam for cell illumination.

3. The illumination apparatus for a cellular analysis apparatus according to claim 1, wherein the reflecting member is one of a metallic member having a flat surface processed as a specular reflecting surface, and a glass plate.

4. The illumination apparatus for a cellular analysis apparatus according to claim 1, further comprising an optical transmission fiber for transmitting the intercepted portion of light reflected by the reflecting member to the photodetector.

5. The illumination apparatus for a cellular analysis apparatus according to claim 1, wherein the feedback controller is constructed so that control of the turning-on states of the LEDs over the preset states is made by adjusting amounts of electric currents supplied to the LEDs.

6. The illumination apparatus for a cellular analysis apparatus according to claim 5, having an overcurrent preventing control function for making control so that overcurrent is prevented from flowing through any of the plurality of LEDs.

7. An illumination apparatus for a cellular analysis apparatus, which is the illumination apparatus supplying the cellular analysis apparatus with illumination light through a common optical path, the illumination apparatus comprising:
   a plurality of LEDs of different center emission wavelengths,
   a photodetector,
   path sharing means for introducing light emitted from the plurality of LEDs into the common optical path,
   light-introducing means located on the common optical path, to introduce partial light out of the light emitted from the plurality of LEDs and travelling along the common optical path into the photodetector,
   a feedback controller for controlling turning-on states of the LEDs over preset states in accordance with an amount of light emitted from the plurality of LEDs and detected by the photodetector, and
   illumination light supplying means located on the common optical path, to supply light that is emitted from the plurality of LEDs, travels along the common optical path and fails to reach the photodetector through the light-introducing means, as illumination light for a cellular analysis,
   wherein the light-introducing means is a reflecting member that reflects the partial light toward the photodetector, and
   wherein a position of the reflecting member relative to the common optical path is adjustable and an amount of the partial light reflected toward the photodetector is adjustable by adjustment of the position of the reflecting member relative to the common optical path.

8. The illumination apparatus for a cellular analysis apparatus according to claim 7, wherein the reflecting member is one of a metallic member having a flat surface processed as a specular reflecting surface, and a glass plate.

9. The illumination apparatus for a cellular analysis apparatus according to claim 7, further comprising an optical transmission fiber for transmitting the partial light reflected by the reflecting member to the photodetector.

10. The illumination apparatus for a cellular analysis apparatus according to claim 7, wherein the feedback controller is constructed so that control of the turning-on states of the LEDs over the preset states is made by adjusting amounts of electric currents supplied to the LEDs.

11. The illumination apparatus for a cellular analysis apparatus according to claim 10, having an overcurrent preventing control function for making control so that overcurrent is prevented from flowing through any of the plurality of LEDs.

* * * * *